United States Patent [19]

Ferrini et al.

[11] Patent Number: 4,608,382
[45] Date of Patent: Aug. 26, 1986

[54] 2-(SULPHINYL AND SULFONYL)-4(5)-PHENYL-5(4)-(3'-PYRIDYL)-IMIDAZOLS

[75] Inventors: Pier G. Ferrini, Binningen; Richard Göschke, Bottmingen, both of Switzerland

[73] Assignee: Ciba-Geigy Corporation, Ardsley, N.Y.

[21] Appl. No.: 588,025

[22] Filed: Mar. 9, 1984

Related U.S. Application Data

[63] Continuation of Ser. No. 321,840, Nov. 16, 1981, Pat. No. 4,461,770, which is a continuation of Ser. No. 200,880, Oct. 27, 1980, abandoned, which is a continuation-in-part of Ser. No. 134,802, Mar. 28, 1980, abandoned, which is a continuation-in-part of Ser. No. 025,310, Mar. 30, 1979, abandoned, and a continuation-in-part of Ser. No. 186,038, May 11, 1980, abandoned.

[30] Foreign Application Priority Data

Apr. 11, 1978 [LU] Luxembourg ................... 79412

[51] Int. Cl.$^4$ .................... A61K 31/44; C07D 401/04
[52] U.S. Cl. .................................... 514/341; 546/278
[58] Field of Search ................. 546/278; 424/263; 514/341

[56] References Cited

U.S. PATENT DOCUMENTS 4,175,127 11/1979 Bender et al. ................. 546/271

Primary Examiner—Jane T. Fan
Attorney, Agent, or Firm—Karl F. Jorda; Michael W. Glynn; Bruce M. Collins

[57] ABSTRACT

Novel substituted 2-mercaptoimidazoles of the formula

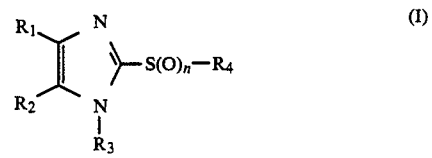

in which at least one of the radicals $R_1$ and $R_2$ is a substituted or unsubstituted heteroaryl group and the other is a substituted or unsubstituted aryl group, $R_3$ is hydrogen or lower alkyl, n is 0, 1 or 2 and $R_4$ is a substituted or unsubstituted aliphatic hydrocarbon radical and their pharmaceutically usable salts exhibit anti-inflammatory, anti-nociceptive and/or antithrombotic activity.

8 Claims, No Drawings

2-(SULPHINYL AND SULFONYL)-4(5)-PHENYL-5(4)-(3'-PYRIDYL)-IMIDAZOLS

This is a continuation of application Ser. No. 321,840, filed on Nov. 16, 1981, issued as U.S. Pat. No. 4,461,770, on July 24, 1984, which is (1) a continuation of Ser. No. 200,880, filed Oct. 27th 1980, now abandoned, which is a continuation-in-part of Ser. No. 134,802, filed Mar. 28, 1980, now abandoned, which is a continuation-in-part of Ser. No. 025,310, filed Mar. 30, 1979, now abandoned, and (2) a continuation-in-part of Ser. No. 186,038, filed May 11th 1980, now abandoned.

The present invention relates to substituted 2-mercaptoimidazoles of the formula

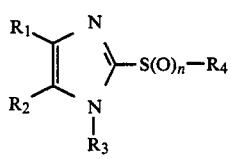

in which at least one of the radicals $R_1$ and $R_2$ is a substituted or unsubstituted heteroaryl group and the other is a substituted or unsubstituted aryl group, $R_3$ is hydrogen or lower alkyl, n is 0, 1 or 2 and $R_4$ is a substituted or unsubstituted aliphatic hydrocarbon radical, and pharmaceutically usable salts, in particular pharmaceutically usable acid addition salts, thereof, processes for their preparation, pharmaceutical preparations containing these compounds or pharmaceutically usable acid addition salts thereof, and the use of the compounds defined above.

In this specification "lower" organic radicals and compounds are to be understood as meaning preferably those which contain not more than 7 and in particular not more than 4 carbon atoms.

Heteroaryl groups are in particular 5-membered heteroaryl radicals which contain one oxygen or sulfur atom, one sulfur atom and one nitrogen atom, or at least two nitrogen atoms, or 6-membered heteroaryl radicals which contain at least one nitrogen atom, the said radicals being bonded via a C atom. Examples are, in particular, furyl, for example 2-furyl, thienyl, for example 2-thienyl, thiazolyl, for example 1,3-thiazol-2-or -4-yl, imidazolyl, for example imidazol-2- or -4-yl, triazolyl, for example 1H- or 2H-1,2,3-triazol-4- or -5-yl or 1H- or 2H-1,2,4-triazol-3- or -5-yl, tetrazolyl, for example 1H-tetrazol-5-yl, pyridyl, for example 2-, 3- or 4-pyridyl, pyrimidinyl, for example 2- or 4-pyrimidinyl, or triazinyl, for example 1,3,5-triazin-2-yl or 1,2,4-triazin-3-yl. Substituents of the said heteroaryl groups are, for example, on carbon atoms, lower alkyl, lower alkoxy, halogen, substituted or unsubstituted amino, trifluoromethyl and/or halogen and/or, on nitrogen atoms, if desired lower alkyl, lower alkoxy-lower alkyl and/or hydroxy-lower alkyl, and also oxy.

Substituted or unsubstituted aryl groups and also aryloxy and arylthio groups are, for example, phenyl, phenoxy and phenylthio groups which are unsubstituted or substituted by lower alkyl, lower alkoxy, halogen, substituted or unsubstituted amino, trifluoromethyl and/or nitro.

Substituted amino groups are monosubstituted or preferably disubstituted amino groups in which the substituents are, for example, lower alkyl, or alkylene which has 4 to 7 ring members and can be interrupted by a nitrogen, oxygen or sulfur atom, such as lower alkylamino, dilower alkylamino and 3-aza-, 3-oxa- or 3-thia-alkyleneamino with, in each case, 5 or 6 ring members. In addition to methylamino and ethylamino, examples are in particular dimethylamino, diethylamino, pyrrolidino, piperidino, morpholino, thiomorpholino, piperazino and N'-lower alkyl-piperazino, for example N'-methylpiperazino.

Aliphatic hydrocarbon radicals are, for example, lower alkyl radicals, which can be unsaturated, such as lower alkyl, lower alkenyl or lower alkynyl.

Substituents of aliphatic hydrocarbon radicals are, for example, substituted or unsubstituted aryl radicals, such as phenyl radicals, or hydroxyl, lower alkoxy, lower alkylthio or substituted or unsubstituted aryloxy, such as phenoxy, or arylthio, such as phenylthio, groups, which are bonded in a position higher than the α-position.

Aliphatic hydrocarbon radicals which are unsubstituted or substituted as indicated are preferably lower alkyl radicals, which can be unsaturated, such as lower alkyl, lower alkenyl or lower alkynyl radicals, and are unsubstituted or substituted by phenyl, which in turn can be substituted, or lower alkyl radicals which are substituted in a position higher than the α-position by hydroxy, lower alkoxy or lower alkylthio or by a substituted or unsubstituted phenoxy or phenylthio group.

Lower alkyl which can be unsaturated and is unsubstituted or substituted by phenyl is, for example, lower alkyl having 1 to 4 C atoms, phenyl-lower alkyl, such as 1- or 2-phenyl-lower alkyl having 7 to 10 C atoms, for example benzyl or 2-phenylethyl, lower alkenyl having 2 to 4C atoms, for example vinyl, allyl or methallyl, phenyl-lower alkenyl having 8 to 10 C atoms, for example styryl, lower alkynyl having 2 to 4 C atoms, for example ethynyl or propargyl, or phenyl-lower alkynyl having 8 to 10 C atoms, for example phenylethynyl.

Hydroxy-lower alkyl is, for example, mono- or dihydroxy-lower alkyl, has in particular 2 to 4 C atoms and is, for example, 2-hydroxyethyl, 2- or 3-hydroxypropyl or 2,3-dihydroxypropyl.

Lower alkoxy-lower alkyl has, for example, 1 to 4 C atoms in each alkyl moiety and is, for example, 2-methoxyethyl, 2-ethoxyethyl or 2- or 3-methoxypropyl.

Lower alkylthio has, for example, 1 to 7 C atoms and is, for example, 2-methylthioethyl.

Phenoxy-lower alkyl has, for example, 1 to 7 C atoms in the alkyl moiety and is, for example, 2-phenoxyethyl; phenylthio-lower alkyl likewise has, for example, 1 to 4 C atoms and is, for example, 2-phenylthioethyl.

Lower alkyl has, for example, 1 to 7 C atoms and is, for example, methyl, ethyl, propyl, isopropyl or n-, iso-, sec.- or tert.-butyl or, less preferentially, one of the isomeric pentyl, hexyl or heptyl groups.

Lower alkoxy has, for example, 1 to 7 C atoms and is, for example, methoxy, ethoxy, propoxy, isopropoxy or n-, sec.-, iso- or tert.-butoxy or, less preferentially, one of the isomeric pentyloxy, hexyloxy or heptyloxy groups.

Lower alkylthio has, for example, 2 to 7 C atoms and is, for example, methylthio, ethylthio, propylthio, isopropylthio or butylthio or, less preferentially, pentylthio, hexylthio or heptylthio.

Lower alkenyl and lower alkynyl have, for example, 2 to 4 C atoms, and lower alkenyl is, for example, vinyl, allyl or methallyl, whilst lower alkynyl is, in particular, ethynyl or propargyl.

Halogen is preferably halogen with an atomic number of not more than 35, such as fluorine, chlorine or bromine.

Salts of compounds of the formula I are in particular pharmaceutically usable acid addition salts with strong acids, such as a mineral acid, for example salts with hydrogen halide acids, in particular hydrochloric acid or hydrobromic acid, i.e. hydrohalides, in particular hydrochlorides and hydrobromides, or sulfuric acid salts, i.e. bisulfates and sulfates.

The invention relates in particular to substituted 2-mercaptoimidazoles of the formula I in which $R_1$, $R_2$, $R_3$ and $R_4$ have the meanings indicated hereinbefore under formula I and n denotes O, and pharmaceutically usable salts, in particular pharmaceutically usable acid addition salts, thereof, processes for their preparation, pharmaceutical preparations containing these compounds or pharmaceutically usable acid addition salts thereof, and the use of the compounds defined above.

The compounds of the formula I have valuable pharmacological properties. In particular, they have a pronounced anti-inflammatory, anti-nociceptive and/or anti-thrombotic activity as well as an inhibitory action on the prostaglandin synthesis. Thus, they prove to have an excellent effect in rats in the kaolin paw oedema test according to Helv. Phydiol. Acta 25, 156 (1967) in the dosage range of about 15 to 150 mg/kg, and also in the Carrageneen paw oedema test according to Di Pasquale et al., Agents and Actions 5, 256 (1975) in the dosage range of about 20 to 200 mg/kg, when administered perorally, in a single dose, additionally also in the adjuvauus-arthritis of the rat on four single doses of about 10 to 60 mg/kg p.o. and in mice in the writhing syndrome induced by phenyl-p-benzoquinone, according to J. Pharmacol. exp. Therap. 125, 237 (1959), in the dosage range of about 30 to 300 mg/kg p.o. and in the emboly of the rabbit lung which had been induced by dosage of arachidonates in a dosis range of about 0,1 to 3 mg/kg p.o..

Furthermore, in the concentration range of about 10 to 30 ml/l, they inhibit in vitro the prostaglandin synthesis from arachidonic acid, demonstrated in the test arrangement according to Prostaglandins 7, 123 (1974).

The compounds of the formula I are therefore outstandingly suitable as active ingredients in pharmaceutical preparations for the treatment of inflammatory diseases, in particular chronic inflammation of the rheumatic type, such as chronic arthritis.

The invention relates primarily to compounds of the formula I in which at least one of the radicals $R_1$ and $R_2$ is substituted or unsubstituted furyl, thienyl, thiazolyl, imidazolyl, triazolyl, tetrazolyl, pyridyl, primidinyl or triazinyl and the other is substituted or unsubstituted phenyl, $R_3$ is hydrogen or lower alkyl, n is 0, 1 or 2 and $R_4$ is an aliphatic hydrocarbon radical which has not more than 7 carbon atoms and is unsubstituted or substituted by unsubstituted or substituted phenyl or, in a position higher than the $\alpha$-position, by hydroxy, lower alkoxy, such as methoxy or ethoxy, lower alkylthio, such as methylthio, or a substituted or unsubstituted phenoxy or phenylthio group, it being possible for ring carbon atoms in the said radicals $R_1$ and $R_2$ as well as phenyl, phenoxy and phenylthio groups to be substituted by lower alkyl, such as methyl, lower alkoxy, such as methoxy or ethoxy, halogen with an atomic number of not more than 35, such as chlorine, trifluoromethyl, nitro and/or amino which is unsubstituted or contains, as substituents, lower alkyl, such as methyl, or 4-membered to 7-membered alkylene, such as trimethylene or tetramethylene, which can be interrupted by nitrogen, oxygen of sulfur, and for ring nitrogen atoms of pyrimidinyl, triazinyl or, in particular, pyridyl radicals also to be substituted by oxy, and their acid addition salts, preferably pharmaceutically usable acid addition salts.

The invention relates in particular to compounds of the formula I in which one of the radicals $R_1$ and $R_2$ is a substituted or unsubstituted pyridyl group and the other is a substituted or unsubstituted phenyl or pyridyl group. $R_3$ is hydrogen or lower alkyl having 1 to 4 C atoms, such as methyl, n is 0 and $R_4$ is lower alkyl having 1 to 7 C atoms which is unsubstituted or substituted by phenyl or, in a position higher than the $\alpha$-position, by hydroxyl, lower alkoxy or lower alkylthio having 1 to 4 C atoms, phenoxy or phenylthio, or is a lower alkenyl or lower alkynyl radical having 2 to 4 C atoms which is unsubstituted or substituted by phenyl, it being possible for pyridyl, phenyl, phenoxy or phenylthio groups to be substituted by lower alkyl having 1 to 4 C atoms, such as methyl, lower alkoxy having 1 to 4 C atoms, such as methoxy or ethoxy, halogen having an atomic number of not more than 35, such as chlorine, nitro, amino or N,N-di-lower alkylamino having 1 to 4 C atoms in each alkyl moiety, such as dimethylamino, and their salts.

The invention preferably relates to compounds of the formula I in which one of the radicals $R_1$ or $R_2$ is pyridyl and the other is phenyl and these radicals independently of one another can be substituted by lower alkyl having 1 to 4 C atoms, such as methyl, lower alkoxy having 1 to 4 C atoms, such as methoxy or ethoxy, halogen having an atomic number of not more than 35, such as chlorine, and/or N,N-di-lower alkylamino having 1 to 4 C atoms in each alkyl moiety, such as dimethylamino, but are preferably unsubstituted, $R_3$ is hydrogen or lower alkyl having 1 to 4 C atoms, such as methyl, n is 0 and $R_4$ is lower alkyl having 1 to 4 C atoms, such as methyl, ethyl, propyl, isopropyl or butyl, lower alkenyl having 2 to 4 C atoms, such as allyl, phenyl-lower alkyl which has 1 to 4 C atoms in the alkyl moiety and is unsubstituted or substituted by lower alkyl having 1 to 4 C atoms, such as methyl, lower alkoxy having 1 to 4 C atoms, such as methoxy or ethoxy, and/or halogen having an atomic number of not more than 35, such as chlorine, hydroxy-lower alkyl which has 1 to 4 C atoms and carries the hydroxyl group or groups in a position higher than the $\alpha$-position, such as 2-hydroxyethyl, or lower alkoxy- or lower alkylthio-lower alkyl which has 1 to 4 C atoms in each alkyl moiety and carries the alkoxy or alkylthio group in a position higher than the $\alpha$-position, such as 2-methoxyethyl or 2-methylthioethyl, and their acid addition salts.

The invention relates in particular to compounds of the formula I in which one of the radicals $R_1$ and $R_2$ is unsubstituted pyridyl, such as 3-pyridyl, or thienyl. such as 2-thienyl, and the other is unsubstituted phenyl or phenyl substituted by lower alkyl having 1 to 4 C atoms, such as methyl, lower alkoxy having 1 to 4 C atoms, such as methoxy, and/or halogen having an atomic number of not more than 35, such as chlorine and in particular fluorine, $R_3$ is hydrogen or, less preferentially, lower alkyl having 1 to 4 C atoms, such as methyl, n is 0, 1 or 2 and $R_4$ is lower alkyl having 1 to 4 C atoms, such as ethyl, and their salts.

The invention relates especially to compounds of the formula I in which one of the radicals $R_1$ and $R_2$ is unsubstituted pyridyl, such as 3-pyridyl, and the other is unsubstituted phenyl or, less preferentially, phenyl substituted by lower alkyl having 1 to 4 C atoms, for example methyl, lower alkoxy having 1 to 4 C atoms, for example methoxy, or halogen, for example chlorine or bromine, $R_3$ is hydrogen or lower alkyl having 1 to 4 C atoms, for example methyl or ethyl, n is 0 and $R_4$ is hydrogen, lower alkyl having 1 to 4 C atoms, for example methyl or ethyl, or hydroxy-lower alkyl which has 2 to 4 C atoms and carries the hydroxyl group in a position higher than the α-position, for example 2-hydroxyethyl, and their acid addition salts.

The invention relates very particularly to compounds of the formula I in which one of the radicals $R_1$ and $R_2$ is pyridyl, such as 3-pyridyl, and the other is phenyl, $R_3$ is hydrogen, n is 0 or 1 and $R_4$ is lower alkyl having 1 to 4 C atoms, such as ethyl, and their acid addition salts.

The invention relates specifically to the compounds of the formula I named in the examples, and their acid addition salts.

The compounds of the formula I and their salts can be prepared by methods known per se, for example by reacting compounds of the formulae

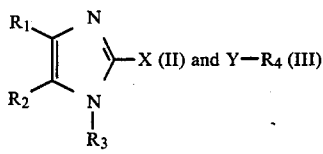

in which one of the radicals X and Y is mercapto, which can be in the form of a salt, and the other is a radical replaceable by etherified mercapto, or one of the radicals X and Y is a group of the formula —S(O)$_n$—Y$_1$, in which Y$_1$ is a reactive esterified hydroxyl group or, if n is 0, an etherified mercapto group or, if n is 1 or 2, an etherified hydroxy group, and the other is a metal radical Y$_2$, with one another, or reacting a compound of the formula II in which X is a mercapto group with an epoxy-lower alkane or with a lower alkene, which is unsubstituted or substituted as indicated, or reacting a compound of the formula II, in which X is a sulfinic acid group in the form of a salt, with a compound of the formula III in which Y is a reactive esterified hydroxyl group and, if desired, converting a resulting compound to another compound of the formula I and/or converting a resulting free compound to an acid addition salt or converting a resulting acid addition salt to the free compound or to another salt.

Mercapto or sulfinic acid groups in the form of a salt are, for example, in the form of an alkali metal salt or ammonium salt, for example mercapto or sulfinic acid groups in the form of the sodium, potassium or ammonium salt.

Radicals X and Y which are replaceable by etherified mercapto are, for example, halogen atoms, for example chlorine, bromine or iodine, and radicals X which are replaceable by the group —SR$_4$ are, furthermore, sulfonyl groups, in particular sulfonyl groups derived from organic sulfonic acids, for example methanesulfonyl, ethanesulfonyl, benzenesulfonyl, p-bromobenzenesulfonyl or p-toluenesulfonyl. Radicals Y which are replaceable by 1-R$_3$-4-R$_1$-5-R$_2$-imidazol-2-ylthio are, furthermore, reactive esterified hydroxyl groups other than halogen, such as hydroxyl groups esterified with sulfuric acid or with an organic sulfonic acid, for example with methane-, ethane-, benzene-, p-bromobenzene- or p-toluene-sulfonic acid.

Reactive esterified hydroxyl groups Y and Y$_1$ are, for example, halogen atoms, such as chlorine, bromine or iodine, or sulfonyloxy groups, preferbly sulfonyloxy groups of the formula —SO$_2$—R$_4$, in groups Y of the formula —S(O)$_n$—Y$_1$, in which n is 2. Etherified mercapto groups Y$_1$ in groups X of the formula —S(O)$_n$—Y$_1$ in which n is 0 are, for example, 1-R$_3$-4-R$_1$-5-R$_2$-imidazol-2-ylthio radicals and in groups Y of the formula S(O)$_n$—Y$_1$ in which n is 0 are, for example, those of the formula —SR$_4$. Etherified hydroxyl is, for example, hydroxyl etherified with an aromatic alcohol, such as a substituted or unsubstituted phenol, in groups of the formula —S(O)$_n$—Y$_1$ in which n is 1, and also lower alkoxy. Metal radicals Y$_2$ are, for example, those of the formulae —M$^I$, —M$^{II}$/2 or —M$^{II}$—Hal, in which M$^I$ is an alkali metal atom, for example lithium or sodium, and M$^{II}$ is an alkaline earth metal atom, for example magnesium, cadmium or zinc.

The reaction can be carried out in a conventional manner, especially in the manner known from the literature for analogous reactions, if necessary in the presence of a catalytic agent, and in the case of the reaction of mercapto compounds of the formula II with alkenes or phenylalkenes, for example in the presence of acid agents, such as Lewis acids, for example of iron-II salts or boron trifluoride, or of peroxides, for example of di-tert.-butyl peroxide, or under the action of UV light, for example with a wavelength of about 200 to 350 um. When carrying out the said reactions, the reaction is in each case preferably carried out in a solvent, and when compounds of the formulae II and III in which one of the radicals X and Y is a metal radical and the other is a group of the formula —S(O)$_n$—Y$_1$ are used as the starting materials, and also in the case of the reaction of mercapto compounds of the formula II with alkenes of phenylalkenes of the formula III, is carried out, for example, in ether, tetrahydrofuran or dioxane, or in the case of the reaction of mercaptans or mercaptides or sulfonic acid salts of the formula II with reactive esters, for example halides, of the formula III is carried out, for example, in an alcohol, for example in methanol, ethanol, ethylene glycol or ethylene glycol monomethyl ether, the reactions in each case advantageously being carried out under an inert gas atmosphere, for example under nitrogen, and if necessary at elevated temperature, for example at the boil.

A preferred embodiment of the above process comprises, for example, reacting a 2-mercapto- or 2-sulfoimidazole derivative of the formula II, which can be in the form of one of the said salts, in a lower alkanol, for example in methanol or ethanol, with a hydrochloric acid, hydrobromic acid, hydriodic acid in sulfuric acid ester of the formula II.

In another preferred embodiment, for example, a compound of the formula II in which X is a metal radical Y$_2$, preferably lithium, and R$_3$ preferably differs from hydrogen, is reacted, for example in an open-chain or cyclic aliphatic ether, for example in diethyl ether, tert.-butyl methyl ether, tetrahydrofuran or dioxan, with a compound of the formula III in which Y is a group of the formula —S—S—R$_4$, halogen—S—R$_4$ or —S(O)$_2$—O—S(O)$_2$—R$_4$.

Some of the starting materials are known. per se.

The compounds of the formula II in which X is mercapto, which have been cited as starting materials, i.e. 1-$R_3$-4-$R_1$-5-$R_2$-2-mercapto-imidazoles and 1-$R_3$-4-$R_1$-5-$R_2$-imidazoline-thiones, in which $R_1$, $R_2$ and $R_3$ are as defined initially under the formula I, can be prepared, for example, by subjecting a compound of the formula

(IV)

in which $X_1$ is a group of the formula —NH—C(=S)—NHR$_3$ and $X_2$ is hydroxyl, or $X_2$ is a group of the formula —NR$_3$—C(=S)—NH$_2$ and $X_1$ is hydroxyl, or a tautomer thereof, which can be in a ketalised form, to intramolecular cyclisation.

Tautomers of compounds of the formula IV are preferably the ketones tautomeric to the enols which have the formula IV. These enols can be ketalised with lower alkanols or lower alkanediols, for example with methanol, ethanol, ethylene glycol or 1,3-propylene glycol.

The intramolecular cyclisation can be carried out in a conventional manner, especially in the manner described in the literature for analogous reactions, for example in a solvent, such as water or an alcohol, for example in water, ethanol, butanol, ethylene glycol or ethylene glycol monomethyl ether, if necessary in the presence of an acid condensing agent, such as a mineral acid, for example hydrochloric acid, and/or at elevated temperature, for example at the boil.

The starting materials of the formula IV, in turn, can be obtained by methods known per se and are advantageously prepared in situ and cyclised without isolation. For this purpose, the starting material used is preferbly a compound of the formula $R_1$—CO—CH(NHR$_3$)—$R_2$ (IVa) or an acid addition salt thereof and this is reacted with thiocyanic acid or a metal thiocyanate. A compound of the formula IV is formed as an intermediate and this cyclises according to the invention. A particularly advantageous reaction is that of a hydrohalide, for example the hydrochloride, of a compound of the formula IVa with an alkali metal thiocyanate or ammonium thiocyanate, such as with sodium thiocyanate or potassium thiocyanate, in aqueous solution, if necessary with warming to 60° to 100° C.

A variant of this process comprises reacting a compound of the formula $R_1$—CH(NH$_2$)—CO—$R_2$ (IVb), or an acid addition salt thereof, with an isothiocyanate of the formula $R_3$—N=C=S (IVc), in an analogous manner.

The starting materials of the formula IV can also be prepared by reacting a compound of the formula $R_o$—CO—CHOH—$R_o$ (IVd), or a compound of the formula $R_o$—CO—CH(halogen)—$R_1$ (IVf) obtainable by α-halogenation, for example with bromine in acetic acid, of a compound of the formula $R_o$—CO—CH$_2$—$R_o$ (IVe), in which formulae one of the groups $R_o$ is the radical $R_1$ and the other is the radical $R_2$ in a conventional manner with a thiourea compound of the formula $R_3$ NH—CS—NH$_2$ (IVg) or a compound which produces the latter in situ, for example a $R_3$-ammonium thiocyanate. At elevated temperatures, for example at 100°-250°, the compound of the formula IV which is first formed cyclises in manner according to the invention. If $R_1$ and $R_2$ are different and $R_3$ is not hydrogen, it is possible, depending on the reactivities of the individual component of the formula IVc and/or on the reaction conditions, to obtain both or only one of the possible isomers, i.e. a 1-$R_3$-4-$R_1$-5-$R_2$-2(3H)-imidazoline-2-thione and/or a 1-$R_3$-4-$R_2$-5-$R_1$-2(3H)-imidzoline-2-thione, and these isomers, can, if necessary, be separated in a conventional manner, for example by fractional crystallization or by chromatography.

The starting materials of the formula IVa, in turn, can be prepared in a manner known per se, for example by converting a compound of the formula $R_1$—CO—CH$_2$—$R_2$ to the oxime, converting the oxime with toluenesulfonyl chloride in pyridine to the oxime-ester, subjecting the latter to the Neber's oxime/amine-ketone rearrangement and, if desired, introducing a radical $R_3$ into the resulting compound of the formula $R_1$—CO—CH(NH$_2$)—$R_2$, for example by reaction with a lower alkyl bromide or lower alkyl iodide.

Starting materials of the formula IVb can be prepared in an analogous manner, using a compound of the formula $R_1$—CH$_2$—CO—$R_2$ as the starting material.

Starting materials of the formula IVd in which $R_1$ and $R_2$ are identical radicals $R_o$ can also be prepared by autocondensation of an aldehyde of the formula $R_0$—CHO (IVh), for example effected with potassium cyanide in ethanol/water or tetrabutyl-ammonium cyanide in water.

The compounds of the formula II in which X is mercapto can also be obtained by heating a corresponding imidazole derivative of the formula

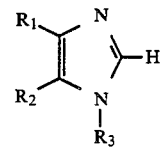

which is unsubstituted in the 2-position, in tetramethylene sulfone with sulfur to about 150°-250° C., for example to about 200° C.

Starting materials of the formula II in which X is a metal radical $Y_2$ are preferably prepared in situ. for example by reacting a compound of the formula V with a metal-organic compound of the formula R—$Y_2$ (VI), in which R is an aliphatic radical, preferably lower alkyl, for example with butyl-lithium or methyl- or butyl-magnesium bromide. Compounds of the formula II in which $Y_2$ is a Zn-halogen or Cd-halogen group can then be obtained from the magnesium-organic compounds thus obtainable, by reaction with zinc chloride or cadmium dichloride.

The starting materials of the formula V can, in turn, be prepared by heating a compound of the formula $R_o$—CO—CH(halogen)—$R_o$ (IVf), in which one of the radicals $R_o$ is a group $R_1$ and the other is a group $R_2$, with formamide, preferably at the boil. The compounds of the formula IVf can, in turn, be obtained by reacting a compound of the formula $R_1$—CH=O or $R_2$—CH=O (Va) in the presence of a di-lower alkylamine hydrochloride, for example dimethylamine hydrochloride, with an alkali metal cyanide, treating the resulting 2—$R_1$— or 2—$R_2$—di-lower alkylaminoacetonitrile (Vb) in dimethylformamide with sodium hydride and then with a compound of the formula $R_2$— or $R_1$—CH$_2$—halogen (Vc), hydrolysing the condensation product by heating for several hours in a mixture of concentrated hydrochloric acid and chloroform and halogenating the resulting compound of the formula $R_o$—CO—CH$_2$—$R_o$ (IVe), for example by means of bromine in acetic acid or copper-II bromide in ethyl acetate.

Starting materials of the formula II in which X is a free or esterified sulfo group or a sulfo group in the form of an anhydride, such as sulfo, lower alkoxy- or phenoxy-sulfonyl or a sulfonyloxysulfonyl group, can be obtained, for example, by oxidising the mercapto group in a compound of the formula II in which X is mercapto to the sulfo group and, if desired, halogenating this, for example with phosphorus pentachloride, and converting the halogenosulfonyl group to esterified sulfo with an alcohol, for example a lower alkanol or phenol, or to an anhydride in the conventional manner, for example by reaction with a sulfonic acid salt. Sulfinic acid esters of the formula II can also be prepared analogously, the oxidation of the mercaptan being stopped at the sulfinic acid stage. Compounds of the formula II in which X is a group —S—S—R$_4$ can be obtained by mild oxidation of mercaptans of the formula II, for example by means of iron-III chloride or atmospheric oxygen.

The compounds of the formula I in which n is 0 can also be prepared by reacting a compound of the formula

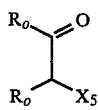

(VI)

in which one of the radicals $R_o$ is a group $R_1$ and the other is a group $R_2$ and $X_5$ is a reactive esterified hydroxyl group, it being possible for a compound of the formula VI in which $R_1$ and/or $R_2$ is a basic group also to be in the form of an acid addition salt, with a N—R$_3$—S—R$_4$—isothiourea, separating a mixture of isomers, which may be obtained, and, if desired, converting the resulting compound to another compound of the formula I and/or converting a resulting free compound to a salt or converting a resulting salt to the free compound or to another salt.

The reaction is carried out in a conventional manner, preferably by liberating the N—R$_3$—S—R$_4$—isothiourea, and if necessary the compound of the formula VII, in situ from a N—R$_3$—S—R$_4$—isothiuronium salt, such as an alkosulfate or halide, for example bromide or chloride, and a compound of the formula VI which may be in the form of a salt, for example by the action of a base, such as an alkali metal hydroxide or alkali metal carbonate, for example sodium hydroxide or carbonate or potassium hydroxide or carbonate, or a nitrogen base, for example ammonia, a tri-lower alkylamine, such as triethylamine or N,N-diisopropylethylamine, or pyridine, 3 equivalents of base being required if the starting materials of the formula VI are in the form of a salt, and otherwise 2 equivalents of base being required, the reaction advantageously being carried out in a solvent, such as a lower alkanol, for example in methanol, ethanol, butanol or amyl alcohol, if necessary at elevated temperature, for example at the boil.

The starting materials of the formula VI can be prepared by methods known per se, for example by reacting a compound of the formula R$_1$—CH=O or R$_2$—CH=O (Va) in the presence of a di-lower alkylamine hydrochloride, for example dimethylamine hydrochloride, with an alkali metal cyanide, treating the resulting 2—R$_1$— or 2—R$_2$—di-lower alkylaminoacetonitrile (Vb) in dimethylformamide with sodium hydride and then with a compound of the formula R$_2$— or R$_1$—CH$_2$—halogen (Vc), hydrolysing the condensation product by heating for several hours in a mixture of concentrated hydrochloric acid and chloroform and halogenating the resulting compound of the formula $R_o$—CO—CH$_2$—$R_o$ (IVe), for example by means of bromine in acetic acid or copper-II bromide in ethyl acetate.

The compounds of the formula I in which R$_3$ is hydrogen can also be prepared by rearranging a compound of the formula

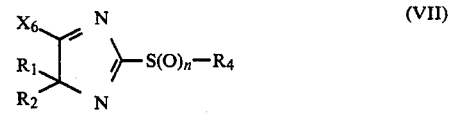

(VII)

in which X$_6$ is mercapto or lower alkylthio, which is unsubstituted or substituted by phenyl, which, in turn, can be substituted as indicated for R$_1$ and R$_2$, for example methylthio or benzylthio.

The rearrangement can be effected in a conventional manner, if necessary in the presence of a catalyst, such as a Lewis acid, for example aluminium trichloride, and advantageously in a solvent, for example in benzene, toluene, N,N-dimethylaniline, anisole, tetralin, chlorobenzene, pyridine or decalin.

The starting materials of the formula VII can be prepared in a manner known per se, for example by first reacting a compound of the formula Vc R$_1$—CO—CO—R$_2$ (VIIa) with thiourea, converting the resulting S—R$_1$—5—R$_2$—2—thiohydantoin with phosphorus pentasulfide to the corresponding 5—R$_1$—5—R$_2$—dithiohydantoin and further reacting the latter with a lower alkyl halide, which can be substituted as indicated for X$_6$.

In resulting compounds of the formula I it is possible, within the scope of the given definition, to introduce, convert or detach substituents.

Thus, for example, an organic radical R$_3$ can be introduced in place of a hydrogen atom R$_3$ by reaction with an agent which introduces the radical R$_3$. Such agents are, for example, reactive esters, such as hydrogen halide acid esters, for example hydrochloric, hydrobromic or hydriodic acid esters, organic sulfonic acid esters, for example methane-, ethane-, benzene-, p-bromobenzene- or p-toluenesulfonic acid esters, or sulfuric acid esters of corresponding alcohols R$_3$OH. The reaction with these agents is carried out in a conventional manner, for example in the presence of a basic condensing agent, such as an alkali metal hydroxide or alkali metal carbonate, for example sodium hydroxide or potassium hydroxide or sodium carbonate or potassium carbonate, an alcoholate, for example an alkali metal lower alkanolate, such as sodium methanolate, and also sodium hydride, advantageously in an inert solvent, for example in dimethylformamide or N-methylpyrrolidone.

Furthermore, in compounds of the formula I, it is possible to carry out N-oxidation on radicals —S(O)$_n$—R$_4$ in which n is 0 to the corresponding sulfinyl or sulfonyl radicals in which n is 1 or 2, of radicals —S(O)$_n$—R$_4$ in which n is 1 to the corresponding sulfonyl radicals in which n is 2 and/or of heteroaryl radicals R$_1$ and/or R$_2$ which have at least one free ring nitrogen atom $\geq$N, such as pyridyl radicals. The oxidation is preferably effected by the action of a suitable oxidising agent, advantageously in a solvent which is inert towards this agent, if necessary with cooling or warming, for example in the temperature range of about −30° to +100° C., preferably at about 0° to 60° C., in a closed vessel and/or under an inert gas, such as nitrogen. Suitable oxidising agents are, for example, peroxy compounds, such as hydrogen peroxide, organic hydroperoxides, for example tert.-butyl hydroperoxide, organic per-acids, such as aromatic or aliphatic percarboxylic acids, for example m-cloroperoxybenzoic acid, peroxyacetic acid or permonophthalic acid, oxidising heavy metal compounds, such as chromium-VI compounds or manganese-IV or manganese-VII compounds, for example chromium trioxide, chromic acid, manganese dioxide or potassium permanganate, oxidising inorganic oxyacids, such as oxyacids of nitrogen, of halogens or of chalcogens, or the anhydrides or salts thereof, for example nitric acid, dinitrogen tetroxide, selenium dioxide or sodium metaperiodate, and also ozone. Suitable solvents are, for example, halogenated hydrocarbons, such as halogenoalkanes, for example carbon tetrachloride, chloroform or methylene chloride, or carboxylic acids, such as alkanoic acids, for example acetic acid, or the anhydrides thereof.

In a preferred embodiment of this oxidation process, it is possible, for example, to oxidise thioethers of the formula I in which n is 0 and/or one of the radicals $R_1$ and/or $R_2$ has an unsubstituted ring nitrogen atom $\geq N$ by reaction with an organic per-acid, for example with m-chloroperbenzoic acid, in a halogenoalkane, for example in chloroform, to the correspnding sulfinyl or sulfonyl compounds in which n is 1 or 2, and, if desired, at the nitrogen atom $\geq N$.

In another preferred embodiment, thioethers of the formula I in which n is 0 can be selectively oxidised by treatment with sodium metaperiodate, preferably in a halogenoalkane, for example in carbon tetrachloride or chloroform, to the corresponding sulfoxides in which n is 1, or the latter can be oxidised with hydrogen peroxide in acetic acid to sulfones in which n is 2.

Conversely, in compounds of the formula I in which n is 1 or 2 and/or heteroaryl radicals $R_1$ and/or $R_2$ are N-oxidised, it is possible to reduce the group —S(O)—$R_4$ or —S(O)$_2$—$R_4$ to the corresponding group S(O)$_o$—$R_4$ and/or to reduce N-oxidised ring nitrogen $\geq N$—O to $\geq N$. The reduction is effected by treatment with customary reducing agents, for example with nascent or catalytically activated hydrogen, such as iron or zinc and acid, such as hydrochloric acid, or with hydrogen in the presence of Raney nickel, advantageously in an inert solvent, such as a lower alkanol, or with light metal hydrides or di-light metal hydrides, for example with alkali metal aluminium hydrides or alkali metal borohydrides, for example with sodium borohydride or lithium aluminium hydride, advantageously in an inert solvent, such as an ether, for example diethyl ether or tetrahydrofuran, or, for selective reduction of $\geq N$—O groups, with a phosphorus-III compound, such as a phospine, for example triphenylphosphine or tri-n-butylphosphine, or a phosphorous acid ester, such as a tri-lower alkyl phosphite, for example with trimethyl phosphite or triethyl phosphite.

Furthermore, it is possible, if desired, to introduce additional C substituents into the radicals $R_1$ and $R_2$ and also into aryl, aryloxy and arylthio groups as constituents of $R_4$. Thus, halogenation can be carried out in a conventional manner, for example by reaction with chlorine or bromine in the presence of iron or by means of N-chlorosuccinimide. Furthermore, alkylation can be carried out in a conventional manner, for example by reaction with an alkyl halide, alkanol or alkene in the presence of aluminium trichloride. Furthermore, nitration can be carried out in a conventional manner, for example by means of nitric acid/sulfuric acid.

Furthermore, nitro groups can be reduced to amino in a conventional manner, such as with nascent hydrogen, for example with iron/hydrochloric acid.

Amino groups can also be substituted in a conventional manner, for example alkylated by reaction with an alkylating agent, such as one of those mentioned, in the presence of a basic condensing agent.

Furthermore, resulting free compounds can be converted to acid addition salts in a manner known per se, for example by reacting a solution of the free compound in a suitable solvent or solvent mixture with one of the abovementioned acids or with a solution thereof, or with a suitable anion exchange resin.

Resulting acid addition salts can be converted to the free compounds in a manner known per se, for example by treatment with a base, such as an alkali metal hydroxide, a metal carbonate or bicarbonate or ammonia, or with a suitable anion exchange resin.

Resulting acid addition salts can be converted to other acid addition salts in a manner known per se, for example by treatment with an anion exchange resin or by treating a salt of an inorganic acid with a suitable metal salt, such as a sodium, barium or silver salt, of an acid in a suitable solvent, in which an inorganic salt which forms is insoluble and thus precipitates out of the reaction mixture.

The compounds, and their salts, can also be obtained in the form of the hydrated or can incorporate the solvent used for crystallisation.

Because of the close relationship between the novel compounds in the free form in the form of their salts, what is stated in this specification in respect of the free compounds or the salts thereof also applies by analogy to the corresponding salts and free compounds.

The invention also relates to those embodiments of the process in which a compound obtainable as an intermediate at any process stage is used as the starting material and the missing process steps are carried out, or in which a starting material is formed under the reaction conditions or is used in the form of a derivative thereof, if desired in the form of a salt.

The starting materials used in the process of the present invention are preferably those which result in the compounds described initially as being particularly valuable.

The pharmaceutical preparations according to the invention, which contain compounds of the formula I or II or pharmaceutically usable salts thereof, are those which are intended for enteral, such as oral or rectal, and parenteral administration and for topical application to warm-blooded animals and which contain the pharmacological active ingredient on its own or together with a pharmaceutically usable carrier. The dosage of the active ingredient depends on the species of warm-blooded animal, the age and the individual condition and also on the mode of administration. In the normal case, an approximate daily dose of about 30–300 mg, advantageously divided into several equal partial doses, is to be estimated for a warm-blooded animal weighing about 75 kg, in the case of oral administration.

The novel pharmaceutical preparations contain, for example, from about 10% to about 80%, and preferably from about 20% to about 60%, of the active ingredient. Pharmaceutical preparations according to the invention for enteral and parenteral administration are, for example, those in the form of dosage units, such as sugar-coated tablets, tablets, capsules or suppositories, as well as ampoules. These are prepared in a manner known per se, for example by conventional mixing, granulating, sugar-coating, dissolving or lyophilising methods. Thus, pharmaceutical preparations for oral use can be obtained by combining the active ingredient with solid carriers, granulating a resulting mixture if desired and processing the mixture or granules, if desired or if necessary after adding suitable adjuncts, to tablets or sugar-coated tablet cores.

Suitable carriers are, in particular fillers, such as sugars, for example lactose, sucrose, mannitol or sorbitol, cellulose preparations and/or calcium phosphates, for example tricalcium phosphate or calcium hydrogen phosphate, and also binders, such as starch pastes, using, for example, maize, wheat, rice or potato starch, gelatin, tragacanth, methylcellulose and/or polyvinylpyrrolidone, and/or, if desired, disintegrators, such as the above starches, and also carboxymethyl starch, cross-linked polyvinylpyrrolidone, agar or alginic acid or a salt thereof, such as sodium alginate. Adjuncts are in particular glidants and lubricants, for example silicic acid, talc, stearic acid or salts thereof, such as magnesium stearate or calcium stearate, and/or polyethylene glycol. Sugar-coated tablet cores are provided with suitable coatings which can be resistant to gastric juices, using, inter alia, concentrated sugar solutions which may contain gum arabic, talc, polyvinylpyrrolidone, polyethylene glycol and/or titanium dioxide, shellack in suitable organic solvents or solvent mixtures, or, for the preparation of coatings resistant to gastric juices, solutions of suitable cellulose preparations, such as acetylcellulose phthalate or hydroxypropylmethylcellulose phthalate. Dyes or pigments can be added to the tablets or the coatings of sugar-coated tablets, for example to identify or indicate different doses of active ingredient.

Further pharmaceutical preparations for oral administration are dry-filled capsules made of gelatin and also soft, sealed capsules made of gelatin and a plasticiser, such as glycerol or sorbitol. The dry-filled capsules can contain the active ingredient in the form of granules, for example in admixture with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers can also be added.

Pharmaceutical preparations for rectal administration are, for example, suppositories, which consist of a combination of an active ingredient with a suppository base. Examples of suitable suppository bases are natural or synthetic triglycerides, paraffinhydrocarbons, polyethylene glycols or high alkanols. Gelatin rectal capsules, which contain a combination of the active ingredient with a base, can also be used; base materials are, for example, liquid triglycerides, polyethylene glycols or paraffinhydrocarbons.

Preparations suitable for parenteral administration are, in particular, aqueous solutions of an active ingredient in a water-soluble form, for example of a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

Pharmaceutical preparations for topical application are, in particular, creams, ointments, pastes, foams, tinctures and solutions, which contain from about 0.5 to about 20% of the active ingredient.

Creams are oil-in-water emulsions which contain more than 50% of water. Substances used as the oleaginous base are, in particular, fatty alcohols, for example lauryl alcohol, cetyl alcohol or stearyl alcohol, fatty acids, for example palmitic acid or stearic acid, liquid to solid waxes, for example isopropyl myristate, wool wax or beeswax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens), and also polyoxyethylene fatty alcohol ethers or fatty acid esters, or corresponding ionic emulsifiers, such as alkali metal salts of fatty alcohol sulfates, for example sodium lauryl-sulfate sodium cetyl-sulfate or sodium stearyl-sulfate, which are customarily used in the presence of fatty alcohols, for example cetyl alcohol or stearyl alcohol. Additives to the aqueous phase are, inter alia, agents which reduce the extent to which the creams dry out, for example polyalcohols, such as glycerol. sorbitol, propylene glycol and/or polyethylene glycols, and also preservatives, perfumes and the like.

Ointments are water-in-oil emulsions which contain up to 70%, but preferably from about 20% to about 50%, of water or aqueous phases. The oleaginous phase comprises, in particular, hydrocarbons, for example petroleum jelly, paraffin oil and/or hard paraffins, which preferably contain hydroxy compounds suitable for improving the water-binding capacity, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerol, propylene glycol, sorbitol and/or polyethylene glycol, and preservatives, perfumes and the like.

Greasy ointments are anhydrous and contain, as the base, in particular hydrocarbons, for example paraffin, petroleum jelly and/or liquid paraffins, and also natural or partially synthetic fat, for example coconut fatty acid triglyceride, or preferably hardened oils, for example hydrogenated groundnut oil or castor oil, and also fatty acid partial esters of glycerol, for example glycerol mono- and di-stearate, and, for example, the fatty alcohols, emulsifiers and/or additives for increasing the absorption of water, which have been mentioned in connection with the ointments.

Pastes are creams and ointments containing secretion-absorbing powder constituents, such as metal oxides, for example titanium oxide or zinc oxide, and talc and/or aluminium silicates, the purpose of which is to bind the moisture or secretion present.

Foams are administered from pressurised dispensers and are liquid oil-in-water emulsions in aerosol form, with halogenated hydrocarbons, such as chlorofluorolower alkanes, for example dichlorodifluoromethane and dichlorotetrafluoroethane, being used as propellants. Substances used as the oleaginous phase are, inter alia, hydrocarbons, for example paraffin oil, fatty alcohols, for example cetyl alcohol, fatty acid esters, for example isopropyl myristate, and/or other waxes. The emulsifiers used are, inter alia, mixtures of those which have primarily hydrophilic properties, such as polyoxyethylene sorbitan fatty acid esters (Tweens) and those which have primarily lipophilic properties, such as sorbitan fatty acid esters (Spans). In addition, the conventional additives, such as preservatives and the like, are used.

Tinctures and solutions in most cases have an aqueous-ethanolic base, to which the following substances are added, inter alia: polyalcohols, for example glycerol, glycols and/or polyethylene glycol, as humectants for reducing evaporation, and fat-restoring substances, such as fatty acid esters with lower polyethylene glycols, i.e. lipophilic substances which are soluble in the aqueous mixture, as a replacement for fatty substances which are removed from the skin with the ethanol, and, if necessary, other adjuncts and additives.

The pharmaceutical preparations for topical use are prepared in a manner known per se, for example by dissolving or suspending the active ingredient in the base or in a part thereof, if necessary. When processing the active ingredient in the form of a solution, it is usually dissolved in one of the two phases before emulsifying, and when processing the active ingredient in the form of a suspension, it is mixed with a part of the base after emulsifying and then added to the remainder of the formulation.

The present invention also relates to the use of the compounds of the formulae I and II, and of the salts of such compounds with salt-forming properties, preferably for the treatment of inflammations, in particular of inflammatory chronic diseases of the rheumatic type, particularly chronic arthritis.

The following examples illustrate the present invention without in any way restricting the scope thereof. Temperatures are in degrees Centigrade.

EXAMPLE 1

0.8 g of sodium is dissolved in 200 ml of ethanol. 8 g of 2-mercapto-4(5)-phenyl-5(4)-(3-pyridyl)-imidazole are added to the solution and the mixture is heated under reflux. After a clear solution has formed, 2.3 ml of 2-chloroethanol are added dropwise and the reaction mixture is heated under reflux for 16 hours. The solvent is evaporated off in vacuo and the residue is partitioned between water and ethyl acetate. The organic phases are washed with water and saturated sodium chloride solution, dried over sodium sulfate and evaporated. Crystalline 2-(2-hydroxyethylthio)-5(4)-phenyl-4(5)-(3-pyridyl)-imidazole is obtained as the residue and after recrystallisation from ethyl acetate/petroleum ether this melts at 128°–130° C.

The starting material can be prepared, for example, as follows.

10.8 g of benzyl 3-pyridyl ketone are stirred together with 40 ml of pyridine and a solution of 8 g of hydroxylamine hydrochloride in 15 ml of pyridine for 6 hours at 100°. The reaction mixture is poured onto ice/water and the resulting mixture is stirred for a further 15 minutes. The crystals which have precipitated are filtered off with suction, washed with water and dried under a high vacuum. Benzyl 3-pyridyl ketone oxime with a melting point of 122°–126° is obtained.

A solution of 7.7 g of p-toluenesulfonyl chloride in 15 ml of pyridine is added dropwise in the course of 5 minutes to a solution, which is stirred at −10°, of 8.5 g of benzyl 3-pyridyl ketone oxime in 20 ml of pyridine. The reaction mixture is placed in a refrigerator for 24 hours and then poured onto ice/water. After some stirring and grinding, the oil which has separated out solidifies to crystals. These are filtered off with suction, washed with water and dried under a high vacuum. Benzyl 3-pyridyl ketone oxime p-toluenesulfonate is obtained and this is employed in the next stage without further purification.

11.6 g of crude benzyl 3-pyridyl ketone oxime p-toluenesulfonate are suspended in 90 ml of absolute ethanol. A solution of 3.7 g of potassium tert.-butylate in 30 ml of absolute ethanol are then added dropwise at 0°, with stirring. The reaction mixture is stirred at 0° for 2 hours. The suspension is filtered with suction and the filtrate, which contains the desired α-amino-benzyl 3-pyridyl ketone, is immediately reacted further in the next stage.

3.6 g of sodium thiocyanate are dissolved in 60 ml of ethanol and 4.5 ml of concentrated hydrochloric acid are added to the solution. The suspension is filtered with suction and the filtrate is heated, together with the alcoholic solution of α-amino-benzyl 3-pyridyl ketone, for 18 hours under reflux. After cooling, crude 2-mercapto-4(5)-phenyl-5(4)-(3-pyridyl)-imidazole can be filtered off, with suction, from the reaction mixture. The filtrate contains further product. The crude product is recrystallised from dimethylformamide/water and then melts at 290°–300°.

EXAMPLE 2

5 g of 2-mercapto-4(5)-phenyl-5(4)-(3-pyridyl)-imidazole are dissolved in 50 ml of methanol and 10 ml of 2N sodium hydroxide solution. 2.85 g of methyl iodide are added dropwise, the mixture is stirred for 2 hours at room temperature, 50 ml of water are added, the resulting mixture is filtered with suction and the residue is washed with water. This yields crude 2-methylthio-4(5)-phenyl-5(4)-(3-pyridyl)-imidazole, which when recrystallised from a mixture of isopropanol and petroleum ether (8:5 parts by volume) melts at 193°–194°.

EXAMPLE 3

8 g of 2-mercapto-4(5)-phenyl-5(4)-(3-pyridyl)-imidazole are dissolved in 40 ml of methanol and 16 ml of 2N sodium hydroxide solution. 4.55 g of methyl iodide are added dropwise to the solution. The mixture is stirred for a further 2 hours at room temperature. 40 ml of water are added, the resulting mixture is filtered with suction and the residue is washed with water. A mixture of 1-methyl-2-methylthio-4-phenyl-5-(3-pyridyl)-imidazole and 1-methyl-2-methylthio-5-phenyl-4-(3-pyridyl)-imidazole is obtained. This mixture can be separated into the components by chromatography. Thus, on a silica gel column, first one component with a melting point of 141°–143° is eluted with chloroform and then the other component with a melting point of 125°–127° is eluted with chloroform/ethyl acetate (8:2 parts by volume).

EXAMPLE 4

The following compounds can also be prepared in a manner analogous to that described in Examples 1–3: 2-(2-hydroxyethylthio)-1-methyl-4-phenyl-5-(3-pyridyl)-imidazole, 2-(2-hydroxyethylthio)-1-methyl-5-phenyl-4-(3-pyridyl)-imidazole, 2-(2-methoxyethylthio)-4(5)-phenyl-5(4)-(3-pyridyl)-imidazole, 2-(2-methoxyethylthio)-1-methyl-4-phenyl-5-(3-pyridyl)-imidazole, 2-(2-methoxyethylthio)-1-methyl-5-phenyl-4-(3-pyridyl)-imidazole, 2-(2-methylthioethylthio)-4(5)-phenyl-5(4)-(3-pyridyl)-imidazole, 1-methyl-2-(2-methylthioethylthio)-4-phenyl-5-(3-pyridyl)-imidazole, 1-methyl-2-(2-methylthioethylthio)-5-phenyl-4-(3-pyridyl)-imidazole, 2-ethylthio-4(5)-phenyl-5(4)-(3-pyridyl)-imidazole, 2-propylthio-4(5)-phenyl-5(4)-(3-pyridyl)-imidazole, 2-isopropyl-4(5)-phenyl-5(4)-(3-pyridyl)-imidazole, 2-methylthio-4,5-bis-(2-thienyl)-imidazole and 2-ethylthio-4,5-bis-(2-thienyl)-imidazole.

EXAMPLE 5

In a manner analogous to that described in Example 2, the following compounds can be prepared using, in each case, 7.6 g of 2-mercapto-4(5)-phenyl-5(4)-(3-pyridyl)-imidazole as the starting material: 2-ethylthio-4(5)-phenyl-5(4)-(3-pyridyl)-imidazole, melting point 196°–198° (from isopropanol/petroleum ether), 2-propylthio-4(5)-phenyl-5(4)-(3-pyridyl)-imidazole, melting point 143°–144° (from isopropanol/petroleum ether) and 2-isopropylthio-4(5)-phenyl-5(4)-(3-pyridyl)-imidazole, melting point 182°–184° (from isopropanol/petroleum ether).

EXAMPLE 6

A solution of 6.3 g of 85% m-chloroperbenzoic acid in 70 ml of chloroform is added dropwise to a suspension of 8 g of 2-methylthio-4(5)-phenyl-5(4)-(3-pyridyl)-imidazole in 400 ml of chloroform, with stirring. The resulting solution is left to stand overnight and is then washed successively with sodium bicarbonate solution and water, dried over sodium sulfate and evaporated to dryness. The residue is twice recrystallised from isopropanol/petroleum ether. 2-Methanesulfinyl-4(5)-phenyl-5(4)-(3-pyridyl)-imidazole with a melting point of 166°–169° is obtained.

Using 2-ethylthio-4(5)-phenyl-5(4)-(3-pyridyl)-imidazole as the starting material, 2-ethanesulfinyl-4(5)-phenyl-5(4)-(3-pyridyl)-imidazole with a melting point of 162°–164° is obtained in an analogous manner.

EXAMPLE 7

8 ml of acetic acid and 0.38 ml of 30% hydrogen peroxide are added to 1.0 g of 2-ethanesulfinyl-4(5)-phenyl-5(4)-(3-pyridyl)-imidazole and the mixture is stirred overnight at 70°. It is allowed to cool, neutralised with sodium hydroxide solution and filtered with suction. This yields 2-ethanesulfonyl-4(5)-phenyl-5(4)-[3-(1-oxidopyridinio)]-imidazole, which meets at 208°–210°.

EXAMPLE 8

2.86 g of α-bromobenzyl 3-pyridyl ketone hydrobromide and 1 g of S-methylisothiuronium bromide are suspended in 30 ml of acetonitrile, 3.1 g of N,N-diisopropylethylamine are added and the mixture is stirred overnight. The reddish orange suspension is filtered and the filtrate is evaporated under reduced pressure. The residue is taken up in chloroform, the chloroform solution is dried over sodium sulfate and evaporated and the residue is recrystallised from chloroform/petroleum ether. 2-Methylthio-4(5)-phenyl-5(4)-(3-pyridyl)-imidazole with a melting point of 193°–194° is obtained.

The starting material can be prepared, for example, as follows:

A solution of 17 g of bromine in 150 ml of acetic acid is added dropwise to 20 g of benzyl 3-pyridyl ketone in 200 ml of acetic acid and the mixture is stirred overnight. The α-bromobenzyl 3-pyridyl ketone hydrobromide which has precipitated is filtered off and can be used without further purification.

EXAMPLE 9

The following compounds can also be prepared in a manner analogous to that described in Examples 1 to 8: 2-ethylthio-4(5)-(p-fluorophenyl)-5(4)-(2-thienyl)-imidazole, m.p. 160°–163°, 2-methylthio-4(5)-(p-fluorophenyl)-5(4)-(2-thienyl)-imidazole, m.p. 131°–133°, and 2-propylthio-4(5)-(p-fluorophenyl)-5(4)-(2-thienyl)-imidazole.

EXAMPLE 10

Tablets containing 25 mg of active ingredient, for example 2-methylthio-4(5)-phenyl-5(4)-(3-pyridyl)-imidazole, can be prepared as follows:

| Constituents (for 1,000 tablets): | |
| --- | --- |
| Active ingredient | 25.0 g |
| Lactose | 100.7 g |
| Wheat starch | 7.5 g |
| Polyethylene glycol 6000 | 5.0 g |
| Talc | 5.0 g |
| Magnesium stearate | 1.8 g |
| Demineralised water | q.s. |

PREPARATION

All the solid ingredients are first forced through a sieve of 0.6 mm mesh width. The active ingredient, the lactose, the talc, the magnesium stearate and half the starch are then mixed. The other half of the starch is suspended in 40 ml of water and this suspension is added to a boiling solution of the polyethylene glycol in 100 ml of water. The resulting starch paste is added to the bulk of the constituents and the mixture is granulated, with the addition of water if necessary. The granules are dried overnight at 35°, forced through a sieve of 1.2 mm mesh width and compressed to tablets which are concave on both sides and about 6 mm in diameter.

Tablets containing, in each case, 25 mg of one of the other compounds of the formula I named in Examples 1 to 4 can also be prepared in an analogous manner.

EXAMPLE 11

Tablets, for chewing, containing 30 mg of active ingredient, for example 2-methylthio-4(5)-phenyl-5(4)-(3-pyridyl)-imidazoline, can be prepared, for example, as follows:

| Composition (for 1,000 tablets): | |
| --- | --- |
| Active ingredient | 30.0 g |
| Mannitol | 267.0 g |
| Lactose | 179.5 g |
| Talc | 20.0 g |
| Glycine | 12.5 g |
| Stearic acid | 10.0 g |
| Saccharine | 1.0 g |

-continued

| Composition (for 1,000 tablets): | |
|---|---|
| 5% gelatin solution | q.s. |

PREPARATION

All the solid ingredients are first forced through a sieve of 0.25 mm mesh width. The mannitol and the lactose are mixed and granulated with the addition of gelatin solution and the granules are forced through a sieve of 2 mm mesh width, dried at 50° and again forced through a sieve of 1.7 mm mesh width. The active ingredient, the glycine and the saccharine are mixed carefully, the mannitol, the lactose granules, the stearic acid and the talc are now added and the whole is mixed thoroughly and compressed to tablets which are concave on both sides, have a diameter of about 10 mm and have a breaking notch on the top.

Tablets for chewing containing, in each case, 30 mg of one of the other compounds of the formula I named in Examples 1 to 4 can also be prepared in an analogous manner.

EXAMPLE 12

Tablets containing 100 mg of active ingredient, for example 2-methylthio-4(5)-phenyl-5(4)-(3-pyridyl)-imidazole, can be prepared as follows:

| Composition (for 1,000 tablets): | |
|---|---|
| Active ingredient | 100.0 g |
| Lactose | 248.5 g |
| Maize starch | 17.5 g |
| Polyethylene glycol 6000 | 5.0 g |
| Talc | 15.0 g |
| Magnesium stearate | 4.0 g |
| Demineralised water | q.s. |

PREPARATION

The solid ingredients are first forced through a sieve of 0.6 mm mesh width. The active ingredient, the lactose, the talc, the magnesium stearate and half the starch are then intimately mixed. The other half of the starch is suspended in 65 ml of water and this suspension is added to a boiling solution of the polyethylene glycol in 260 ml of water. The resulting paste is added to the pulverulent substances and the whole is mixed and granulated, if necessary with the addition of water. The granules are dried overnight at 35°, forced through a sieve of 1.2 mm mesh width and compressed to tablets which are concave on both sides, are about 10 mm in diameter and have a breaking notch on the top.

Tablets containing 100 mg of another compound of the formula I according to Example 1 can also be prepared in an analogous manner.

EXAMPLE 13

Tablets containing, in each case, 25 or 100 mg of a compound according to one of Examples 5 to 8, and tablets for chewing containing 30 mg of a compound according to one of Examples 5 to 8, can also be prepared in a manner analogous to that described in Examples 10 to 12.

EXAMPLE 14

In an analogous manner as described in Examples 1 to 8 also 2-ethanesulphinyl-4(5)-(4-fluorophenyl)-5(4)-(2-thienyl)-imiazole, m.p. 143°-145°, 2-ethanesulphonyl-4(5)-(4-fluorophenyl)-5(4)-(2-thienyl)-imidazole, m.p. 180°-182°, 2-ethansulfonyl-4(5)-phenyl-5(4)-(3-pyridyl)-imidazole, 2-isopropylthio-4(5)-(p-methoxy-phenyl)-5(4)-(4-pyridyl)-imidazole, m.p. 206°-208°, 2-isopropylthio-4(5)-(p-fluorophenyl)-5(4)-(4-pyridyl)-imidazole, m.p.-262°-263°, 2-isopropanesulfonyl-4(5)-(p-methoxyphenyl)-5(4)-(4-pyridyl)-imdazole, m.p. 180°, 2-(2-hydroxyethylthio)-4,5-bis-(2-pyridyl)-imdazole (m.p. of hydropromide 247°-249°), 2-(2-hydroxyethyl-thio)-4,5-bis-(2-thienyl)-imdiazole, m.p. 123°-125°, 2-(2-hydroxyethanesulfinyl)-4,5-bis-(2-thienyl)-imidazol, m.p. 97° and 2-(2-hydroxyethanesulfonyl)-4,5-bis-(2-thienyl)-imidazole, m.p. 102°-103°, can be manufactured.

EXAMPLE 15

A suspension of 15 g of 2-ethylthio-4(5)-phenyl-5(4)-(3-pyridyl)-imdazole in 15 ml of ethanol is acidified to pH=1 by means of an ethanolic solution of hydrochloride acid, instantanously yielding a clear solution. Then, diethyl ether is added, until precipitation begins. The crystals formed are filtered off and recrystallised twice from ethanol yielding 2-ethylthio-4(5)-phenyl-5(4)-(3-pyridyl)-imidazole bis-hydrochloride of m.p. 174°-176°.

EXAMPLE 16

To a suspension of 2,8 g 2-ethylthio-4(5)-phenyl-5(4)-(3-pyridyl)-imidazole in 20 ml of methanol a solution of 1,92 g of methansulfonic acid in 15 ml of ethanol is added, yielding a clear, yellowish solution. This solution is evaporated to dryness, and the residue is crystallised by trituration with a mixture of isopropanol and hexane, yielding 2-ethylthio-4(5)-phenyl-5(4)-(3-pyridyl)-imidazole bis-methanesulfonate of m.p. 150°-152° (decomp.)

What is claimed is:

1. A compound selected from the group consisting of (i) a 2-sulfinyl-4(5)-phenyl-5(4)-(pyrid-3-yl)-imidazole of the formula:

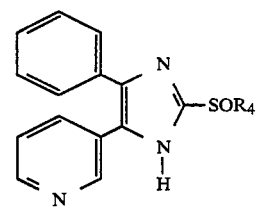

wherein $R_4$ is methyl or ethyl;

(ii) a 2-sulfonyl-4(5)-phenyl-5(4)-(pyrid-3-yl)imidazole of the formula:

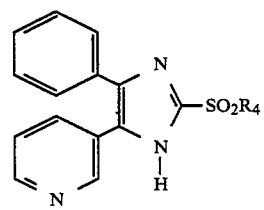

wherein $R_4$ is methyl or ethyl;
(iii) the N-oxides thereof; and
(iv) the pharmaceutically acceptable salts thereof.

2. A compound according to claim 1 wherein $R_4$ is methyl.

3. A compound according to claim 1 wherein $R_4$ is ethyl.

4. A compound according to claim 1 which is 2-methanesulfinyl-4(5)-phenyl-5(4)-(pyrid-3-yl)imidazole.

5. A compound according to claim 1 which is 2-ethanesulfinyl-4(5)-phenyl-5(4)-(pyrid-3-yl)imidazole.

6. A compound according to claim 1 which is 2-ethanesulfonyl-4(5)-phenyl-5(4)-(pyrid-3-yl)imidazole.

7. The method of producing an analgesic and anti-inflammatory response in a warm blooded animal which comprises administering thereto an effective amount of a compound according to claim 1.

8. A pharmaceutical preparation comprising an amount of a compound according to claim 1 sufficient upon administration to a warm blooded animal to produce an analgesic or anti-inflammatory effect, and a pharmaceutical carrier.

* * * * *